United States Patent [19]

Gilson et al.

[11] Patent Number: 5,055,629

[45] Date of Patent: Oct. 8, 1991

[54] PROCESS FOR ISOMERIZING HYDROCARBONS

[75] Inventors: Jean-Pierre Gilson; Johannes M. Nanne; Gerrit J. den Otter, all of Amsterdam, Netherlands

[73] Assignee: Shell Oil Company, Houston, Tex.

[21] Appl. No.: 520,429

[22] Filed: May 8, 1990

[30] Foreign Application Priority Data

May 15, 1989 [GB] United Kingdom ............... 8911077

[51] Int. Cl.$^5$ .............................................. C07C 5/13
[52] U.S. Cl. ................................................. 585/739
[58] Field of Search ........................................ 585/739

[56] References Cited

U.S. PATENT DOCUMENTS

| | | | |
|---|---|---|---|
| 3,326,797 | 6/1967 | Young | 208/111 |
| 3,507,931 | 4/1970 | Morris et al. | 260/683.65 |
| 4,703,025 | 10/1987 | Kokotailo et al. | 502/60 |
| 4,788,378 | 11/1988 | Chang et al. | 585/739 |

FOREIGN PATENT DOCUMENTS 55046 6/1982 European Pat. Off. .

OTHER PUBLICATIONS

Treacy et al., "Two New Three-Dimensional Twelve--Ring Zeolite Frameworks of Which Zeolite Beta is a Disordered Intergrowth", Nature, vol. 332, pp. 249-251, 1988.

*Primary Examiner*—Curtis R. Davis

[57] ABSTRACT

Process for isomerizing hydrocarbons at elevated temperature and pressure in the presence of hydrogen by contacting said hydrocarbons with a catalyst comprising zeolite beta and a hydrogenating-dehydrogenating metal and/or a compound of a hydrogenating-dehydrogenating metal, which zeolite beta has been treated with a solution having a pH of at least 9 and which catalyst has been calcined.

12 Claims, No Drawings

PROCESS FOR ISOMERIZING HYDROCARBONS

FIELD OF THE INVENTION

The present invention relates to a process for isomerizing hydrocarbons at elevated temperature and pressure in the presence of hydrogen by contacting said hydrocarbons with a catalyst comprising zeolite beta and a hydrogenating-dehydrogenating metal and/or a compound of a hydrogenating-dehydrogenating metal.

BACKGROUND OF THE INVENTION

It is well known that catalysts based on mordenite are useful in isomerizing hydrocarbons. Catalysts based on mordenite which has been treated with an acid solution show especially good results when applied in those processes, as is described in e.g. U.S. Pat. No. 3,507,931. As zeolite beta is, like mordenite, a large-pore zeolite, it would be expected that zeolite beta when treated with an acid solution would give good results when applied in a hydroisomerization process. However, it was observed that a treatment with an acid solution did not improve the performance of zeolite beta, but even deteriorated it.

It has now been found that zeolite beta when treated with a solution having a pH of at least 9 does not only have higher activity and selectivity in hydroisomerization processes than untreated zeolite beta, but even shows better results than mordenite-based catalysts which are used commercially.

SUMMARY OF THE INVENTION

The present invention therefore provides a process for isomerizing hydrocarbons at elevated temperature and pressure in the presence of hydrogen by contacting said hydrocarbons with a catalyst comprising zeolite beta and a hydrogenating-dehydrogenating metal and/or a compound of a hydrogenating-dehydrogenating metal, which zeolite beta has been treated with a solution having a pH of at least 9 and which catalyst has been calcined.

DESCRIPTION OF THE PREFERRED EMBODIMENTS

A description of the crystal structure of zeolite beta can be found in the article by M. M. J. Treacy and J. M. Newsam, Nature 332, pp 249–251 (1988), which article is incorporated herein by reference. Any zeolite having the essential structural features of zeolite beta can be used in principle, e.g. zeolite Nu-2 as described in European Pat. No. 55,046. Zeolite beta is normally prepared from a solution containing at least silica, alumina and a template.

Zeolite beta can be used for preparing a catalyst according to the present invention, with part or all of the template still present or with the template removed by e.g. calcination. The treatment of zeolite beta with a solution having a pH of at least 9 is suitably carried out on a zeolite beta of which the template has been removed.

A zeolite beta which is especially suitable for preparing a catalyst according to the present invention, is a zeolite beta which is essentially free of ammonium-ions before deposition of the hydrogenating-dehydrogenating metal(s) and/or compound(s) thereof. This can be accomplished e.g. by calcining zeolite beta before the deposition of the hydrogenating-dehydrogenating metal(s) and/or compound(s) thereof.

It is understood that the expression "a hydro-genating-dehydrogenating metal and/or a compound of a hydro-genating-dehydrogenating metal" refers to metal(s), metal-ion(s) and/or compound(s) containing metal(s) and/or metal-ion(s), and any combination thereof which show hydrogenating-dehydrogenating activity.

The solution having a pH of at least 9 can contain any compound giving the solution its suitable pH value, e.g. an organic and/or inorganic basic compound and/or a salt of such basic compound. Suitably the compound is a hydroxide-containing compound, e.g. sodium hydroxide or ammonium hydroxide. Solutions having a pH of at least 11 are very suitable for use in the present invention. Any suitable solvent as well as any suitable mixture of solvents can be used to prepare the solution having a pH of at least 9.

Calcination of zeolite beta, suitably preceded by drying, can be carried out after treatment with the solution having a pH of at least 9 or after deposition of the hydrogenating-dehydrogenating metal(s) and/or compound(s) of the hydrogenating-dehydrogenating metal(s) on the treated zeolite beta. Suitably the modified zeolite beta is calcined after deposition of the hydrogenating-dehydrogenating metal(s) and/or compound(s) of a hydrogenating-dehydrogenating metal(s).

The calcination is normally carried out at a temperature below 800° C., e.g. between 200° and 700° C., preferably at a temperature between 450° and 650 ° C.

The catalyst used in the process according to the invention can be used without binder or can comprise a mixture of zeolite beta and binder, in which mixture the binder suitably is present in an amount ranging from 5 to 90% by weight (wt %) and the zeolite beta in an amount ranging from 95 to 10 wt %, based on total amount of zeolite beta and binder. The binder can be added to zeolite beta before or after treatment with the solution having a pH of at least 9. The binder present in the catalyst suitably comprises inorganic refractory oxide(s), crystalline material(s) or a mixture thereof. Both amorphous and crystalline binders can be applied. Examples of suitable binders comprise silica, alumina, silica-alumina, clays, zirconia, magnesia, silica-zirconia, titania and silica-boria. Preference is given to the use of alumina as a binder.

Furthermore, in the process of the present invention any other well known hydroisomerization catalyst, e.g. mordenite-based hydroisomerization catalysts, can be used in combination with the catalyst containing treated zeolite beta, suitably such that treated zeolite beta is present in an amount ranging from 20 to 80 wt % and the other hydroisomerization catalyst is present in an amount ranging from 80 to 20 wt %. Different kinds of catalysts can be used e.g. when mixed together physically or prepared by co-crystallization. Different catalysts can be present in different, separate reactors which are placed in series.

The catalyst used in the process according to the invention comprises suitably one or more hydrogenating-dehydrogenating metal(s) or one or more compound(s) of hydrogenating-dehydrogenating metal(s) or mixtures thereof; suitable metals are metals of Group VIII of the Periodic Table of the Elements, such as nickel, platinum and palladium. Preferably the catalyst comprises one or more noble metals from Group VIII, such as platinum and/or palladium. The amount of metal present in the catalyst suitably is between 0.01 and 10.0 wt % of metal calculated on zeolite beta; the amount of noble metal(s) present suitably is between 0.01 and 5.0 wt %, preferably between 0.02 and 2.0 wt %, particularly between 0.05 and 1.0 wt %. The hydrogenating-dehydrogenating metal(s) or compound(s) thereof can be deposited on the catalyst in any suitable way, e.g. by impregnation, ion-exchange, precipitation or co-mulling.

The process according to the present invention can be applied to a wide variety of hydrocarbons, including hydrocarbons suitable for use as lubricating base oils or components thereof. The process is particularly suited for isomerizing relatively light components, i.e. hydrocarbons or mixtures of hydrocarbons containing from 4 to 10 carbon atoms, preferably containing from 5 to 7 carbon atoms.

The process according to the present invention can be carried out at a temperature between 175° and 325° C., suitably between 200° and 275° C., and a pressure between 5 and 100 bar, suitably between 10 and 50 bar, preferably between 15 and 35 bar, and a hydrogen/feed molar ratio of between 0.1 and 10 mole/mole.

After isomerization has taken place part or all of the hydrocarbon mixture obtained in the process according to the present invention, may be subjected to a separation treatment such as a distillation, in order to obtain the product(s) wanted., suitably, certain fractions of the product(s) obtained in the process can be recycled.

The present invention will now be illustrated by means of the following Examples.

EXAMPLE 1

A commercially available, essentially template-free zeolite beta was treated, in accordance with the prcocess according to the invention, at a temperature of 50° C. for 1 hour with a solution containing 0.10 mol of sodium hydroxide per liter of water and was afterwards washed with a solution containing ammonium nitrate to substantially remove the sodium ions. The zeolite beta thus obtained was then impregnated with the help of a solution containing platinum ions. The dried powder obtained was shaped into small pellets and calcined at a temperature of 550° C. during 2 hours. This catalyst, containing 0.4% wt of platinum, is hereinafter called catalyst A.

EXAMPLE 2

The experiment described in Example 1 was repeated, but using a solution containing 0.01 mol of sodium hydroxide per liter of water. The catalyst thus obtained is hereinafter called catalyst B.

EXAMPLE 3

The experiment described in Example 1 was repeated but using, for comparative purposes, a solution containing 1 mol of hydrogen chloride per liter water, at reflux conditions. The catalyst thus obtained is hereinafter called catalyst C.

EXAMPLE 4

The catalysts as described above and an untreated zeolite beta containing 0.4 wt % of platinum (catalyst D), and a commercial catalyst based on mordenite which had been treated with an acid solution (catalyst E), were used in an isomerization process wherein a feedstock consisting of 60 wt % of n-pentane, 35 wt % of n-hexane and 5 wt % of cyclohexane, was contacted with the appropriate catalysts at a temperature of 260° C., a pressure of 25 bar, a weight hourly space velocity of 1.7 kg/kg/h and a hydrogen/feed molar ratio of 1.25 mole/mole. The experiment was carried out in once-through operation.

The isomerization activity for $C_5$- and $C_6$-paraffins was determined for each catalyst and expressed as the percentage of iso-pentane in the $C_5$-product and of 2,2-dimethylbutane in the $C_6$-product, respectively.

The results obtained are given in Table 1, wherein the relative activity of catalyst E has been defined as 1.0 for the respective iso-pentane and butane products.

TABLE 1

| Catalyst | $C_5$-isomerization Activity | $C_6$-isomerization Activity |
| --- | --- | --- |
| A | 1.1 | 1.2 |
| B | 1.1 | 1.2 |
| C | 0.2 | 0.1 |
| D | 0.5 | 0.3 |
| E | 1.0 | 1.0 |

What is claimed is:

1. A process for isomerizing paraffinic hydrocarbons at elevated temperature and pressure in the presence of hydrogen by contacting said hydrocarbons with a catalyst comprising zeolite beta in combination with a metal selected from the group consisting of a hydrogenating-dehydrogenating metal, a compound of a hydrogenating-dehydrogenating metal, and mixtures theeof, wherein said zeolite beta has been treated with a solution having a pH of at least about 9 and said catalyst has been calcined.

2. The process of claim 1, wherein the solution having a pH of at least about 9 contains a hydroxide-containing compound.

3. The process of claim 2, wherein the hydroxide-containing compound is sodium hydroxide and/or ammonium hydroxide.

4. The process of claim 1 or 2, wherein the solution has a pH of at least about 11.

5. The process of claim 1, wherein zeolite beta has been calcined at a temperature below about 800° C.

6. The process of claim 5, wherein zeolite beta has been calcined at a temperature of between about 450° C. and about 650° C.

7. The process of claim 1, wherein the hydrogenating-dehydrogenating metal is a metal of Group VIII of the Periodic Table of the Elements.

8. The process of claim 7, wherein the hydrogenating-dehydrogenating metal is selected from the group consisting of platinum, palladium and mixtures thereof.

9. The process claim 7 or 8, wherein the amount of metal of Group VIII of the Periodic Table of the Elements present is between about 0.01% by weight and about 5.0% by weight of metal basis the amount of zeolite beta.

10. The process of claim 7 or 8, wherein the amount of metal of Group VIII present is between about 0.05% by weight and about 1.0% by weight of metal basis the amount of zeolite beta.

11. The process of claim 1, wherein the process is carried out at a temperature between about 175° C. and about 325° C. and a pressure between about 5 and about 100 bar.

12. The process of claim 1, wherein the hydrocarbons which are subjected to said isomerization process comprise hydrocarbons having 4 to 10 carbon atoms.

* * * * *